(12) United States Patent
Sakhinana et al.

(10) Patent No.: US 12,387,083 B2
(45) Date of Patent: Aug. 12, 2025

(54) SYSTEM AND METHOD FOR MOLECULAR PROPERTY PREDICTION USING HYPERGRAPH MESSAGE PASSING NEURAL NETWORK (HMPNN)

(71) Applicant: Tata Consultancy Services Limited, Mumbai (IN)

(72) Inventors: Sagar Srinivas Sakhinana, Pune (IN); Sri Harsha Nistala, Pune (IN); Venkata Sudheendra Buddhiraju, Pune (IN); Venkataramana Runkana, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 976 days.

(21) Appl. No.: 17/498,005

(22) Filed: Oct. 11, 2021

(65) Prior Publication Data

US 2023/0037388 A1 Feb. 9, 2023

(30) Foreign Application Priority Data

Jul. 16, 2021 (IN) .............................. 202121032176

(51) Int. Cl.
*G06N 3/04* (2023.01)
*G06F 9/50* (2006.01)
*G06F 9/54* (2006.01)
*G06F 18/214* (2023.01)
(Continued)

(52) U.S. Cl.
CPC ............. *G06N 3/04* (2013.01); *G06F 9/5044* (2013.01); *G06F 9/546* (2013.01);
(Continued)

(58) Field of Classification Search
CPC ............ G06N 3/02; G06N 3/04; G06N 3/042; G06N 3/08; G06N 20/00; G16C 20/30;
(Continued)

(56) References Cited

U.S. PATENT DOCUMENTS

2019/0139622 A1* 5/2019 Osthege .................. G16B 5/20
2019/0303535 A1* 10/2019 Fokoue-Nkoutche ......................
G06F 17/16
(Continued)

FOREIGN PATENT DOCUMENTS

CN 112070277 A 12/2020
CN 112417219 A 2/2021

OTHER PUBLICATIONS

Withnall et al., "Building attention and edge message passing neural networks for bioactivity and physical-chemical property prediction", Jan. 8, 2020, pp. 1-18 (Year: 2020).*
(Continued)

*Primary Examiner* — Tamara T Kyle
*Assistant Examiner* — William Wong
(74) *Attorney, Agent, or Firm* — Finnegan, Henderson, Farabow, Garrett & Dunner, LLP (57) ABSTRACT

This disclosure relates generally to system and method for molecular property prediction using hypergraph message passing neural network (HMPNN). Typical MPNN architectures used for chemical graphs representation learning have limitations, including, inefficiency to learn long-range dependencies for homogeneous graphs, ineffectiveness to model topological properties of graphs taking into consideration the multiscale representations, and lack of anti-smoothing weighting mechanism to address graphs random walk limit distribution. Disclosed method and system HyperGraph attention-driven Hypergraph Convolution. The Hypergraph attention driven convolution, on molecular hypergraph results in learning efficient embeddings on the high-order molecular graph-structured data. By taking into account the transient incidence matrix, the induced inductive bias augments the scope of molecular hypergraph representation learning.

9 Claims, 5 Drawing Sheets

(51) Int. Cl.
  *G06N 3/042* (2023.01)
  *G06N 3/08* (2023.01)
  *G16C 20/30* (2019.01)
  *G16C 20/70* (2019.01)

(52) U.S. Cl.
  CPC ......... *G06F 18/2155* (2023.01); *G06N 3/042* (2023.01); *G06N 3/08* (2013.01); *G16C 20/30* (2019.02); *G16C 20/70* (2019.02)

(58) Field of Classification Search
  CPC ... G16C 20/70; G06F 18/2155; G06F 9/5044; G06F 9/546
  See application file for complete search history.

(56) References Cited

U.S. PATENT DOCUMENTS

| | | | |
|---|---|---|---|
| 2020/0285944 A1* | 9/2020 | Lee | G06F 18/24 |
| 2021/0158127 A1* | 5/2021 | Ren | G06N 3/045 |
| 2021/0398621 A1* | 12/2021 | Stojevic | G16C 10/00 |

OTHER PUBLICATIONS

Arya et al., "HyperSAGE: Generalizing Inductive Representation Learning on Hypergraphs," (2020), 13 pages.

Bai et al., "Hypergraph Convolution and Hypergraph Attention," (2020), 30 pages.

Ding et al., "Be More with Less: Hypergraph Attention Networks for Inductive Text Classification," (2020), 10 pages.

Garasuie et al., "Improving Hypergraph Attention and Hypergraph Convolution Networks," (2021), 7 pages.

Kaist et al., "A Hypergraph Convolutional Neural Network for Molecular Properties Prediction using Functional Group," (2021), 16 pages.

Yadati, "Neural Message Passing for Multi-Relational Ordered and Recursive Hypergraphs," (2020), 15 pages.

Yin et al., "DyHCN: Dynamic Hypergraph Convolutional Networks," (2021), 10 pages.

Zhang et al., "Learnable Hypergraph Laplacian for Hypergraph Learning," (2021), 5 pages.

\* cited by examiner

SYSTEM AND METHOD FOR MOLECULAR PROPERTY PREDICTION USING HYPERGRAPH MESSAGE PASSING NEURAL NETWORK (HMPNN)

PRIORITY CLAIM

This U.S. patent application claims priority under 35 U.S.C. § 119 to: India Application No. 202121032177, filed on Jul. 16, 2021. The entire contents of the aforementioned application are incorporated herein by reference.

TECHNICAL FIELD

This disclosure relates generally to molecular property predictions, and more particularly to system and method for molecular property prediction using Hypergraph Message Passing Neural Network (HMPNN).

BACKGROUND

The prediction of molecular properties is a fundamental task in the field of drug discovery. The prediction can be done by a variety of computational methods that significantly accelerate the overall process of finding better drug candidates in a time and cost-efficient manner. Machine learning technique, in specific, supervised learning on drug-like potential molecules has remarkable applications for use in more effective drug discovery. It provides substantial prospects in diminishing the computational complexity which is a key desideratum for prognostication of molecular properties and aid in billion price tag cost reduction of developing a potential drug for treatment.

Typically, Convolution Neural Networks (CNNs) and its variant structured neural network architectures obtain dimensionality reduction and extract dominant features for molecular properties prediction tasks by performing spatial convolutions on Euclidean domains. The CNNs input is obliged to, therefore, have a regular and grid-like structure. This restriction hampers the utilization of CNN's to numerous scientific disciplines, where irregular graph structure or manifold data are commonly accessible.

To deal with the all too often non-grid-like data structures, Graph Neural Networks (GNNs), are popularly been looked upon as a noteworthy modeling framework, to perform inference on graph data. GNNs learn hidden representations of nodes, subgraphs, and the whole input graph by synchronous message-aggregation from node neighborhood by following through computational graph of the nodes. These learned hidden representations are rotation and translation invariant. Graph Neural Network (GNN) or its subsequent improvised variants are effective algorithms for learning the discriminative node embeddings of the arbitrary sized, graph-structured data by utilizing the relational inductive biases that are shared across the non-Euclidean graph domain. These low-dimensional representations of each node entities serve as feature inputs for graph-pooling, to evaluate the graph-level embeddings and aid in graph based inductive (semi-supervised) or rather for transductive (supervised) learning tasks.

In a known study, the one-hop node neighborhood permutation-invariant (independent on the arbitrary ordering of nodes) message-aggregation (spatial graph convolution) was utilized to transform the node representations, and a Graph Convolutional Network (GCN) was presented. The algorithm exemplified state-of-the-art results in metrics concerning the semi-supervised classification tasks. Another study revealed GCNs ability to relational reasoning. Yet another study presented a coalesce framework through a function-setting invariant message-passing and read-out phase. Each node in the graph sends neural messages to its local-node neighborhood based on its hidden states and overhauls its hidden states established on the aggregated message received from its immediate adjoining neighbors through the edge-type connecting them as overlapping partitions of the original graph. Still another study presented a unique and distinct neural message-aggregation and node embeddings update algorithmic approach to evaluate a representation of the entire input complex topology molecular graphs. By leveraging message passing neural networks (MPNNs) on open-sourced datasets, a state-of-the-art performance was achieved and a benchmark for predicting molecular properties was established. However, alternative models in the MPNN foster family set can be introduced that can complement with a decrease in time complexity, thereby yielding a considerable drop in resource consumption over previous MPNNs for computation of low dimensional node embeddings in comparison with the baselines.

Molecular graphs are discrete, non-linear data structure and irregular in size. Message Passing Neural Networks (MPNN's) a machine-learning computer algorithm for non-linear structured data by intrinsically treating drug-like organic molecules as topological molecular graphs as input, learn a probabilistic graphical model motivated message-passing schemes.

The MPNN architectures assist in the chemical graphs representation learning when solved for inductive learning tasks. However, based on theoretical guarantees in geometric deep learning, the expressive power of the state-of-the-art message-passing schemes is limited. The drawbacks are to (1) its inefficiency to learn long-range dependencies for homogeneous graphs. (2) Its ineffectiveness to model topological properties of graphs taking into consideration the multiscale representations. (3) Lack of anti-smoothing weighting mechanism to address graphs random walk limit distribution.

SUMMARY

Embodiments of the present disclosure present technological improvements as solutions to one or more of the above-mentioned technical problems recognized by the inventors in conventional systems. For example, in one embodiment, a processor implemented method for molecular property prediction using a hypergraph message passing neural network (HMPNN) is provided. The method includes accessing a database comprising information associated with a plurality of molecules, via one or more hardware processors. Each molecule of the plurality of molecules represented as a molecular graph. Further the method includes representing each of the molecular graph as an undirected hypergraph, via the one or more hardware processors, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix. Furthermore, the method includes learning, in a plurality of iterations, a dynamic transient incidence matrix through a hypergraph-attention mechanism between a node and a set of hyperedges associated with the node of the hypergraph to perform a hyper-graph convolution using the HMPNN, via the one or more hardware processors. Learning the dynamic transient incidence matrix through the hypergraph-attention mechanism in an iteration from amongst the plurality of iterations includes performing attention over each node of a set of nodes from amongst the plurality of nodes with a first set of feature vectors associated with a hyperedge within a local-intra neighborhood of the node to compute a plurality of intra-hyperedge neural-message aggregations. Performing the attention within the local-intra neighborhood of the node comprises evaluating a first transient incidence matrix; updating a set of hidden state vectors for each node of the set of nodes in the hyperedge by utilizing the plurality of intra-hyperedge neural-message aggregations; performing attention over each node from amongst the set of nodes with a second set feature vectors associated with a set of inter-hyperedges within a global-inter neighborhood of the node to compute a plurality of inter-hyperedge neural-message aggregations, wherein performing the attention within the global-inter neighborhood of the node comprises evaluating a second transient incidence matrix; and updating the set of hidden state vectors of each nodes from amongst the set of nodes based on the plurality of inter-hyperedge neural-message aggregations of the node. Moreover, the method includes performing, via the one or more hardware processors, a hypergraph pooling on the set of hidden state vectors using a read-out function to determine a hypergraph level vector representation. Also, the method includes applying, via the one or more hardware processors, a linear layer on hypergraph-level vector representation to compute the molecular properties, via the one or more hardware processors.

In another aspect, a system for molecular property prediction using a hypergraph message passing neural network (HMPNN) is provided. The system includes a memory storing instructions; one or more communication interfaces; and one or more hardware processors coupled to the memory via the one or more communication interfaces, wherein the one or more hardware processors are configured by the instructions to access a database comprising an information associated with a plurality of molecules, wherein each molecule of the plurality of molecules represented as a molecular graph. Further, the one or more hardware processors are configured by the instructions to represent each of the molecular graph as an undirected hypergraph, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix. Furthermore learn, in a plurality of iterations, a dynamic transient incidence matrix through a hypergraph-attention mechanism between a node and a set of hyperedges associated with the node of the hypergraph to perform a hyper-graph convolution using the HMPNN. To learn the dynamic transient incidence matrix through the hypergraph-attention mechanism in an iteration from amongst the plurality of iterations, the one or more hardware processors are configured by the instructions to perform attention over each node of a set of nodes from amongst the plurality of nodes with a first set of feature vectors associated with a hyperedge within a local-intra neighborhood of the node to compute a plurality of intra-hyperedge neural-message aggregations, wherein performing the attention within the local-intra neighborhood of the node comprises evaluating a first transient incidence matrix; update a set of hidden state vectors for each node of the set of nodes in the hyperedge by utilizing the plurality of intra-hyperedge neural-message aggregations; perform attention over each node from amongst the set of nodes with a second set feature vectors associated with a set of inter-hyperedges within a global-inter neighborhood of the node to compute a plurality of inter-hyperedge neural-message aggregations, wherein performing the attention within the global-inter neighborhood of the node comprises evaluating a second transient incidence matrix; and update the set of hidden state vectors of each nodes from amongst the set of nodes based on the plurality of inter-hyperedge neural-message aggregations of the node. The one or more hardware processors are configured by the instructions to perform a hypergraph pooling on the set of hidden state vectors using a read-out function to determine a hypergraph level vector representation; and apply a linear layer on hypergraph-level vector representation to compute the molecular properties.

In yet another aspect, there are provided one or more non-transitory machine-readable information storage mediums comprising one or more instructions which when executed by one or more hardware processors cause accessing a database comprising information associated with a plurality of molecules, via one or more hardware processors. Each molecule of the plurality of molecules represented as a molecular graph. Further the method includes representing each of the molecular graph as an undirected hypergraph, via the one or more hardware processors, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix. Furthermore, the method includes learning, in a plurality of iterations, a dynamic transient incidence matrix through a hypergraph-attention mechanism between a node and a set of hyperedges associated with the node of the hypergraph to perform a hyper-graph convolution using the HMPNN, via the one or more hardware processors. Learning the dynamic transient incidence matrix through the hypergraph-attention mechanism in an iteration from amongst the plurality of iterations includes performing attention over each node of a set of nodes from amongst the plurality of nodes with a first set of feature vectors associated with a hyperedge within a local-intra neighborhood of the node to compute a plurality of intra-hyperedge neural-message aggregations. Performing the attention within the local-intra neighborhood of the node comprises evaluating a first transient incidence matrix; updating a set of hidden state vectors for each node of the set of nodes in the hyperedge by utilizing the plurality of intra-hyperedge neural-message aggregations; performing attention over each node from amongst the set of nodes with a second set feature vectors associated with a set of inter-hyperedges within a global-inter neighborhood of the node to compute a plurality of inter-hyperedge neural-message aggregations, wherein performing the attention within the global-inter neighborhood of the node comprises evaluating a second transient incidence matrix; and updating the set of hidden state vectors of each nodes from amongst the set of nodes based on the plurality of inter-hyperedge neural-message aggregations of the node. Moreover, the method includes performing, via the one or more hardware processors, a hypergraph pooling on the set of hidden state vectors using a read-out function to determine a hypergraph level vector representation. Also, the method includes applying, via the one or more hardware processors, a linear layer on hypergraph-level vector representation to compute the molecular properties, via the one or more hardware processors.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Geometric Deep learning on non-Euclidean domains has found extensive applications to address real-world scenarios by extending state-of-the-art deep learning architectures onto graph structured/manifold data. Graph-based solutions in a multitude of diverse fields including but not limited to systems to optimize delivery, recommendation systems, social networks, manufacturing and supply-chain logistics, knowledge graphs, and information retrieval. Gated recurrent units (units) and long short-term memory (LSTM), are in practice existing architectures utilized in modeling sequential data that extend the memory of recurrent neural networks. RNNs are extended onto the graphs. Graph RNNs apprehend recursive and regular succession motifs of graphs. Graph RNNs are classified based on the operating level as either node-level or rather at the whole graph level.

Graph RNNs categorized as node-level RNNs address node-focused tasks where patterns lie at the node-level for node classification, and recommendation. Graph Neural Networks (GNNs) is a typical example of node-level RNNs which are modeled by low-dimensional hidden characteristic vectors of nodes. Graph-level RNNs describe patterns at the whole graph level. Graph-level RNNs abstract the epitome of the graph and address the graph-focused tasks such as multi-set graph multi-classification, predicting diverse graph properties, and graph generation.

Graph-level RNNs for graph generation capture the time dynamics of the formation of nodes and edges for dynamic graphs & comprehend the sequential network motifs at unlike degrees of graph granularities, and essentially, the generation of nodes and edges in an autoregressive approach respectively. Graph Convolution Neural Networks (GCNs) gain an understanding of the local node-neighborhood and coarse-grained network motifs of graphs through well-designed spatial convolutions. GCNs take into account the node neighborhoods which transform only the node's representations. The learnt node embeddings effectively encapsulates the graph structure information and node features in their respective one-hop neighborhood. GCNs is an effective message-passing framework for representation learning of graphs. Inspired by the attention mechanism a graph attention network (GAT) introduces the attention mechanism into GCNs by modifying the convolution operation by weighing nodes of importance. Jumping knowledge networks (JK-Nets) by jumping all the representations of nodes representations to the final output is an additional mechanism that further improves GCNs performance.

Aforementioned variants of GCNs utilize only vertex features and task-relevant sub-graph or whole level graph structures. The additional information of the edge features is not looked upon in great detail. In a known work, distinct parameters established based on the edge types were trained and leveraged to the downstream graph classification task with an appropriate choice of graph coarsening algorithm which considers the edge features. The autoencoder (AE) and its variations have been widely applied in unsupervised learning tasks and are suitable for learning node representations for nonlinear low-rank manifold structure data such as graphs.

Combinatorial optimization on graphs has drawn increased attention and interest in the machine-learning community which aids in discovering optimal configurations in discrete search spaces where comprehensive enumeration is intractable in divergent fields of transportation, retail, and manufacturing. A knowledge graph obtains and amalgamates information into an ontology and puts in a reasoner to extract brand new knowledge. Google augments its search engine's outcome with information accumulated from diverse sources (Google Knowledge Graph Search API2). Recent works include message passing networks for large-scale knowledge graph reasoning and, estimate node importance for reasoning on knowledge graphs. In recommendation systems, a subclass of information filtering systems, work up to date has looked upon based on algorithmic approaches as either content-based or collaborative filtering recommendation systems. Knowledge-based recommender systems that are based on explicit knowledge (what item shall be recommended based on known given context) is proposed as an alternative where cold start in computer-based information systems is addressed in great detail. Recent works are the graph convolution on knowledge graphs networks for recommendation systems, attention network for the recommendation, web-scale recommender systems and, for social recommendation. Noteworthy graph-based natural language processing and information retrieval based recent studies are graph neural networks for Question Answering, Graph-to-Sequence Learning, for information extraction, for text generation, for text summarization, for relation extraction and, for text classification. Recent advances in Deep learning algorithmic approaches on the Euclidean domain have been extended for molecular property prediction task on graph-structured data.

Deep learning on graphs approaches is subclassified as either transductive (otherwise semi-supervised) or as inductive (otherwise supervised) tasks. In inductive inference tasks, specified a training sub-sample $\{t_y^x\}k_{=1}^N \subseteq T^X$. The model learns to output for which a target is known, $T^Y$. $f: T^X \rightarrow T^Y$; $t_y^x \rightarrow t_k^y$ which can potentially generalize to instances that aren't perceived before or present in training data. In transductive inference tasks, the training dataset has m labeled data points $(t_1^x, t_1^y), \ldots (t_m^x, t_m^y)$ and n unlabeled data points $(t_{m+1}^x, \ldots, t_{m+n}^y)$ where $t_y^x \in \mathbb{R}^d$. Here, d is the characteristic dimension of the graph-level representation. $1 \leq j \leq m+n$ is the input of a labeled otherwise unlabeled data point and $t_j^y \in \{-1,1\}$, $1 \leq j \leq m+n$; is the label type of a labeled data point. The objective here is to predict the label of unlabeled data points.

Message Passing Neural Networks (MPNN) framework merges several distinct and unique contemporary models that exist in the literature. The MPNNs are an abstraction of a non-spectral approach-based graph convolution neural networks. The MPNNs operate on undirected chemical graphs, $\mathcal{G}^M = (\mathcal{V}^M, \mathcal{E}^M)$.

Let $\mathcal{N}^M (|\mathcal{V}^M|)$ denote the number of nodes and $E^M$ ($\mathcal{E}^M$) represents the number of edges for a homogenous chemical graph, $\mathcal{G}^M$. $\mathcal{G}^M$ is described by a set of node features, $N^M \in R^{|\mathcal{V}^M| \times \mathbb{C}}$, $N_i^M \in R^{1 \times \mathbb{C}} \forall i \in \mathcal{V}^M$ and edge features $e_{ij}^M \in R^{|\mathcal{E}^M| \times \mathbb{Z}}$, $\forall (i,j) \in \mathcal{E}^M$. Here, i & $j \in \mathcal{V}^M$ refer to the neighboring nodes of the chemical graph and are connected by an arbitrary edge, $(i,j) \in \mathcal{E}^M \leftrightarrow (j,i) \in \mathcal{E}^M$, $\forall j \in \mathcal{N}(i)$. The chemical graph connectivity $\mathcal{G}^M = (\mathcal{V}^M, \mathcal{E}^M)$ is given by the adjacency matrix, $\mathcal{G}_A^M$. Molecules are represented as annotated undirected chemical graphs. The atoms are considered to be the nodes of the chemical graphs. The bonds connecting adjacent atoms in the chemical graphs correspond to edges. The MPNN framework is leveraged in this particular scientific discipline for mathematical modeling of the drug-like organic molecules. It helps to gain insight and assists in the description of the chemical graph's topology into a characteristic representation of the entire chemical graphs to later aid in the molecular property prediction task. Based on the graph's connectivity, an incident edge in between two neighboring atoms in the chemical compound (or nodes in a chemical graph) acts as both arriving and departing edge tagged by the same label (bond type).

Figure 1A:
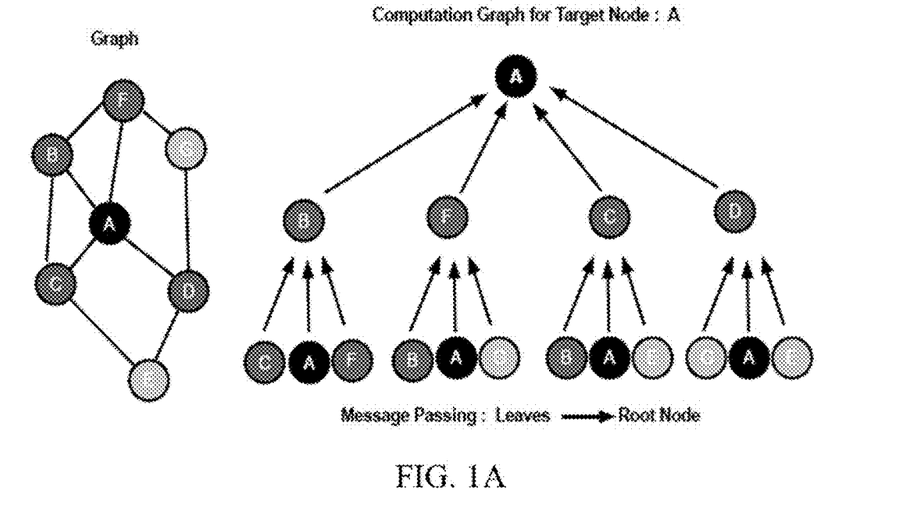
FIG. 1A illustrates a representation of message passing phase of a conventional message passing neural network (MPNN).
Figure 1B:
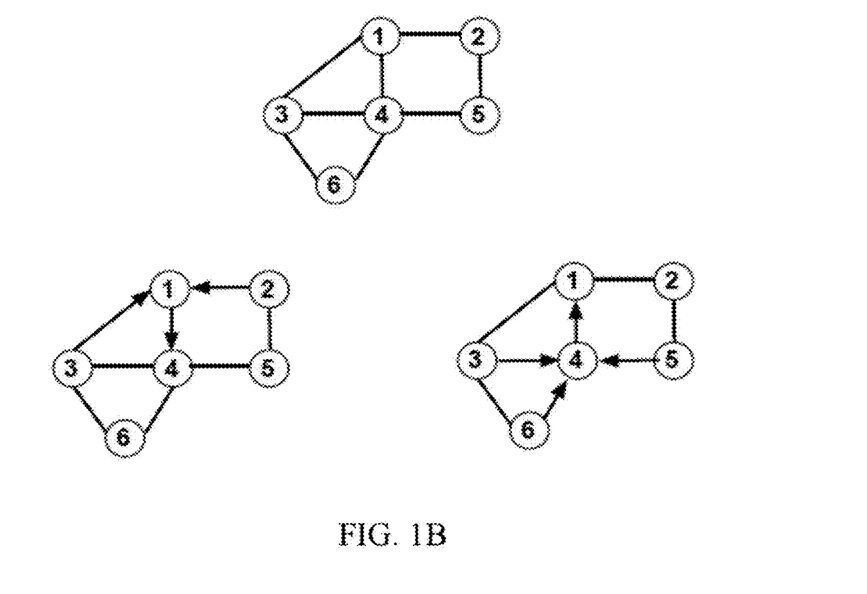
FIG. 1B illustrates a representation of readout phase of a conventional message passing neural network (MPNN).

The MPNNs forward pass consists of two phases—a message passing phase (illustrated in FIG. 1A) and a readout phase (illustrated in FIG. 1B). The message passing phase generates neural messages and update node representations by aggregating encoded information of node's embeddings from confined graph neighborhood. A permutation invariant readout phase is leveraged to perform graph pooling. Readout phase function takes an adjacency matrix $\mathcal{G}_A^M$ as input and satisfies the following property, $\mathcal{F}(P\mathcal{G}_A^M P^T) = \mathcal{F}(\mathcal{G}_A^M)$. Here, P is a permutation matrix. The message propagation utilizes the distinct message generating functions acting on the undirected chemical graph topology $M_{in}^f$ and $M_{out}^f$ represents the universal function approximator for the generation of neural messages received through a particular edge type and propagated from the same edge-type between the nodes of the chemical graphs, respectively. Based on the direction of the edge under consideration, that particular transformation function is put into operation on the edge, $e_{ij}^M$. The MPNNs forward pass communicates messages as described by a computational graph for every target node from the bottom (leaf) node to the top (root) node by iterating for T computational time steps. These outgoing messages are evaluated for every edge by transforming the source node's hidden state according to the edge feature vector.

Identical edge-type incident on different node neighbors, which is characterized by distinct edge feature vectors share with the same instance of the message generating neural-network function. Each node in the molecular graph aggregates neural messages (message-pooling operation) from its local T-hop neighbors, as determined from $\mathcal{G}_A^M$ and the received messages are perceived by the target node by performing mathematical computations to update its hidden representation. This message-passing scheme assists in learning effective discriminative hidden representations of the nodes in the chemical graphs, by adopting a Back-propagation through time (BPTT) learning algorithm for training the MPNNs framework when solved for graph-based inductive learning tasks. The MPNNs are synchronous message-passing systems. They update all messages in parallel. In the end, each edge between the vertices in the chemical graph have messages evaluated in both directions from the source to sink and contrariwise. The message passing phase is described by utilizing a message generating function, $M^f$, and node-embedding update neural network function, $V^f$. $M^f$ and $V^f$ might take possession of diverse in specific to be at variance with function settings. During the span of the message passing phase, the node-level embedding $h_i^t$ of every unique vertex in the molecular graph as given by its computational graph are overhauled and assembled on structural and feature information embedded messages $m_i^{t+1}$, received from its one-hop neighbors as depicted by, $$m_i^{t+1} = \Sigma_{j \in N(i)} M^f(h_j^t, e_{ji}^M) \quad (1)$$

$$h_i^{t+1} = V^f(h_i^t, m_i^{t+1}) \quad (2)$$

Here, $\Sigma_{j \in N(i)}$ depicts the aggregation of neural-information embedded messages over the local one-hop neighborhood of the node, $i \in \mathcal{V}^M$ in the chemical graph, $\mathcal{G}^M$. Here, $h_i$ is learned with the MPNN model parameters through a representative function of the entire input graph when solved for addressing supervised graph regression tasks such as molecular graph property prediction. The readout phase of the MPNN framework performs graph-pooling through set-pooling approach by determining a discriminative graph embedding for the entire input molecular graph by utilizing a differentiable node-reordering invariant neural network function, $R^f$ according to, $\hat{y} = R^f(\{h_i^T | i \in \mathcal{V}^M (\mathcal{G}^M)\}$. $M^f$, $V^f$, and $R^f$ are differentiable neural network functions and have learnable parameters. Mini-Batching with an MPNN with batch size as a hyper-parameter results in the faster training and augments performance of the graph-based deep learning algorithm. It is viable here in this context as it initiates and propagates neural messages across several molecular graphs with varying numbers of vertices $|\mathcal{V}^M|$ and $|\mathcal{E}^M|$. The feature representation of the vertices in the molecular graph, $\mathcal{G}^M$ is denoted by, data.x. data.edgeindex describes the edge indices of source and sink vertices of the edge under consideration and vice-versa. data.edgeattr represents the static edge attributes. data.y is the pre-determined DFT-evaluated properties (ground-truth) for the chemical graphs. The discrepancy between the MPNN model output (estimated) and the true values are measured by the mean-squared error loss function for this graph-based supervised regression task. The Edge-Conditioned Convolution Networks (ECCN) is described by, $h_i^{t+1}=\wedge h_i^t+\Sigma_{j\in N(i)}h_j^t\cdot\Omega_\wedge(e_{ij}^M)$ Here, $\Omega_\wedge$ denotes a multilayer perceptron, parameterized by $\wedge$. The aggregated vector message perceived by the sink node, i is described by $m_i^{t+1}=\Sigma_{j\in N(i)}h_j^t\cdot\Omega_\wedge(e_{ij}^M)$. The MPNN framework message-generating neural-network function is described by, $M^f(h_j^t,e_{ij}^M)=h_j^t\cdot\Omega_\wedge(e_{ij}^M)$. The vertex update function is described by, $V^f(h_i^t,m_i^{t+1}):GRU(h_i^t,m_i^{t+1})$. Here, GRU is a known Gated Recurrent Unit. The hidden state of the previous state is given by, $V^f(h_i^t,m_i^{t+1})$: $GRU(h_i^t,m_i^{t+1})$.

Here, n denotes the total number of nodes in the chemical graphs in a given batch size. $d_m$ & $d_h$ are the characteristic dimension of neural messages and node attributes respectively. Here, the reset gate, $R_t$, $Z_t$, $h_i^t$, $\tilde{h}_i^t$ are evaluated as, $$R_t=\sigma(m_i^{t+1}W_r+h_i^tW_{rh}+b_r), \quad (3)$$

$$Z_t=\sigma(m_i^{t+1}W_z+h_i^tW_{zh}+b_z) \quad (4)$$

$$\tilde{h}_i^t=\tan h(m_i^{t+1}W_h+(R_t\odot h_i^t)W_{hh}+b_n) \quad (5)$$

$$h_i^{t+1}=Z_t\odot h_i^t+(1-Z_t)\odot\tilde{h}_i^t \quad (6)$$

Here, $W_r$, $W_z$, $W_{\tilde{h}}\in\mathbb{R}^{d_m\times d_h}$, $W_{rh}$, $W_{zh}$, $W_{hh}\in\mathbb{R}^{d_h\times d_h}$ are the weight parameters, $b_r$, $b_z$, $b_{\tilde{h}}\in\mathbb{R}^{1\times d_h}$ are the bias.

The graph-level global pooling neural network is evaluated as $$\hat{y}=R^f(\{h_i^T|i\in\mathcal{V}^{\mathcal{M}}(\mathcal{G}^{\mathcal{M}})\}):set2set(\{h_i^T|i\in\mathcal{V}^{\mathcal{M}}(\mathcal{G}^{\mathcal{M}})\} \quad (7)$$

| Algorithm: Message Passing Neural Networks (MPNN) |
| --- |
| 1: Input Feature Training set: data:x; data:edgeindex; data:edgeattr |
| 2: Input Target Label : data:y |
| 3: Regularization Term: Apply dropout on data.x, data.edgeindex, data.edgeattr |
| 4: Message-Passing Phase |
| 5: for t ≤ T do |
| 6: Forward Pass: Perform Edge-Conditioned Convolution |
| 7: Vertex Update: Update hidden states through a GRU |
| 8: end for |
| 9: Read out Phase: Apply Set2Set algorithm |
| 10: Linear Layer (Predict DFT target properties) |
| 11: Return Graph level output |

The MPNN however leads to over-smoothing of learnable embeddings for vertices with higher valency. Various embodiments described herein provides a method and system for molecular property prediction using hyperedge MPNN (HMPNN) in a manner that can alleviate the expressivity of the GCN by leveraging the hyperedge-information in the graph structure of the molecules. Further, the disclosed method and system preventing over-smoothing of learnable embeddings for vertices with higher valency, as will be explained further in the description below.

Figure 2A:
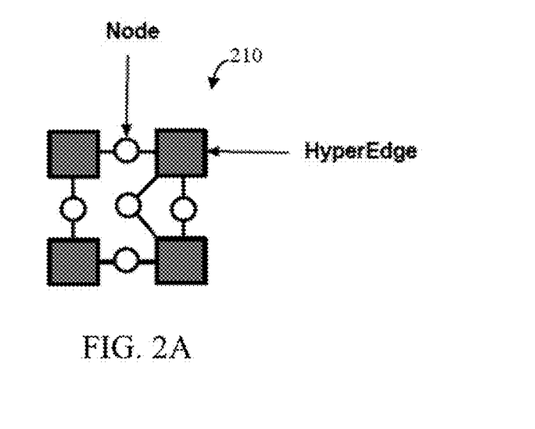
FIG. 2A illustrates a hypergraph according to some embodiments of the present disclosure.

As illustrated with respect to FIG. 2A, a hypergraph 210 is viewed as a generalization of the graph. Given a hypergraph $\mathcal{H}=(V^H,\varepsilon^H)$, where a hyperedge $e_i^H=\{v_1^H, v_2^H, \ldots, v_k^H\}$ can connect multiple vertices. It is in contradiction to an edge in a graph that associates by connecting two adjacent nodes. Superscript, H here applies to hypergraphs. A k-regular hypergraph has each node to have a degree k. The edge connecting two nodes in the chemical/molecular graph, is associated with an edge label and it is the bond type. Herein, in various embodiments a molecule is represented as a hypergraph. Here the hyperedge is the atom and the node is considered to be a bond. To guarantee an alteration between a graph and a hypergraph, each node in the molecular hypergraph has degree 2 (2-regular). The label on a hyperedge dictates the nodes it has (referred to as valence). A hypergraph is illustrated and explained further with reference to FIGS. 2B-2C.

Figure 2B:
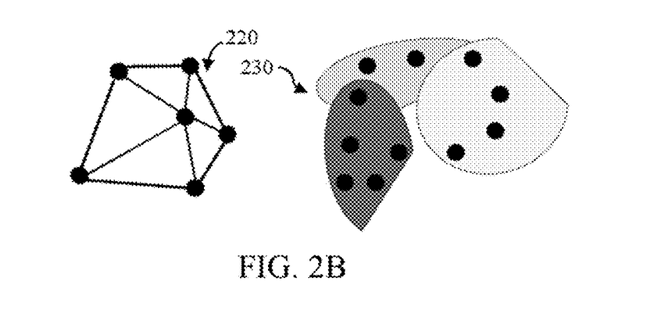
FIG. 2B illustrates a molecular graph and a hyper-graph according to some embodiments of the present disclosure.

Referring to FIG. 2B, a simple graph 220 and a hypergraph 230 are illustrated. In the graph 220, every edge at most connects two nodes. In the hypergraph 230, each hyperedge represented by a color shade eclipse connects furthermore than two vertices.

Figure 2C:
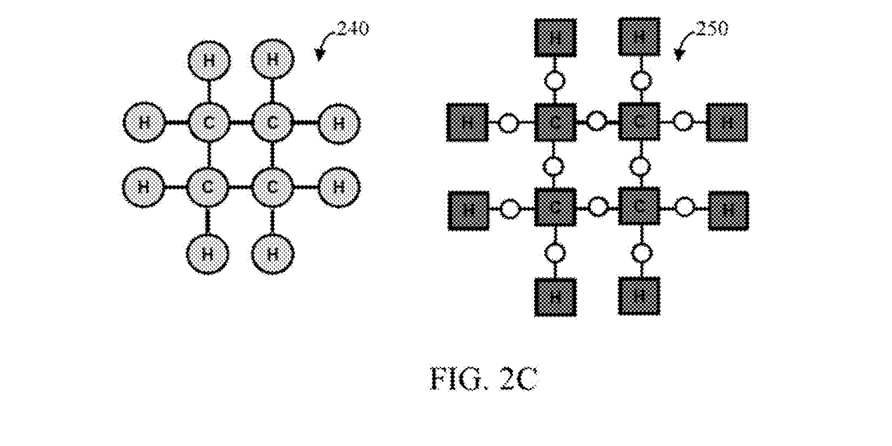
FIG. 2C illustrates a molecular graph and a corresponding undirected hypergraph according to some embodiments of the present disclosure.

Recent advances in deep learning on graphs proposed spatial graph convolutions are designed to take a molecular graph $\mathcal{G}=(V^G,\varepsilon^G)$ as input. Here, $V^G=\{x_1^G, x_2^G, \ldots x_M^G\}$ describes the node-set. $\varepsilon^G\subseteq V^G\times V^G$ represents the edge set adjacency matrix of the molecular graph is given by $A^G\in\mathbb{R}^{M\times M}$, where M denotes the $|V^G|$. The edge describes the pairwise relationship as stated in the explicitly known connectivity structure between two neighboring vertices $x_1^G$ and $x_2^G$. FIG. 2C illustrates a molecular graph 240 and a corresponding undirected hypergraph 250.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Figure 3:
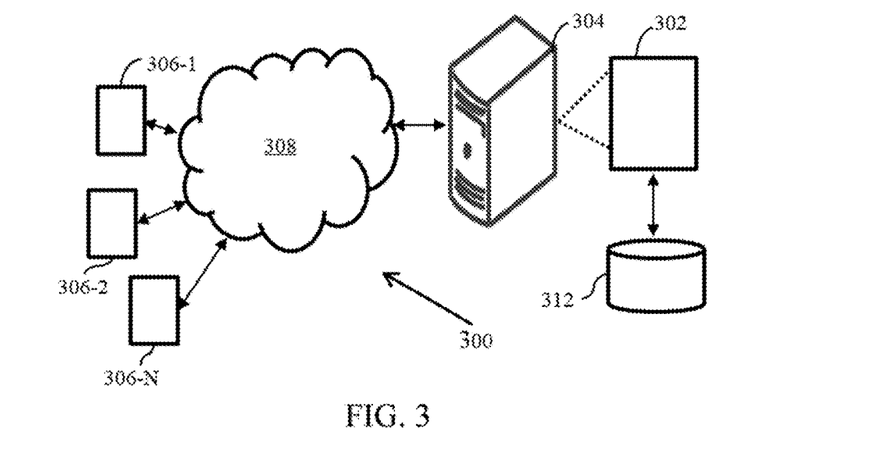
FIG. 3 illustrates a network implementation of a system for molecular property prediction using hypergraph message passing neural network (HMPNN) according to some embodiments of the present disclosure.
Figure 4A:
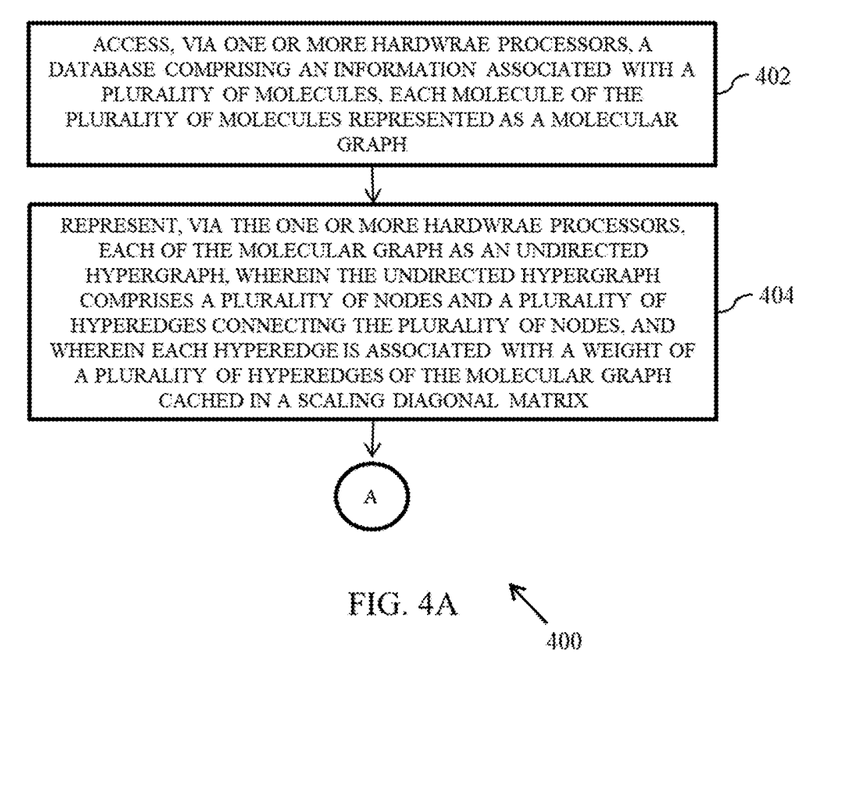
FIGS. 4A and 4B is a flow diagram illustrating a method for molecular property prediction using HMPNN in accordance with some embodiments of the present disclosure.
Figure 4B:
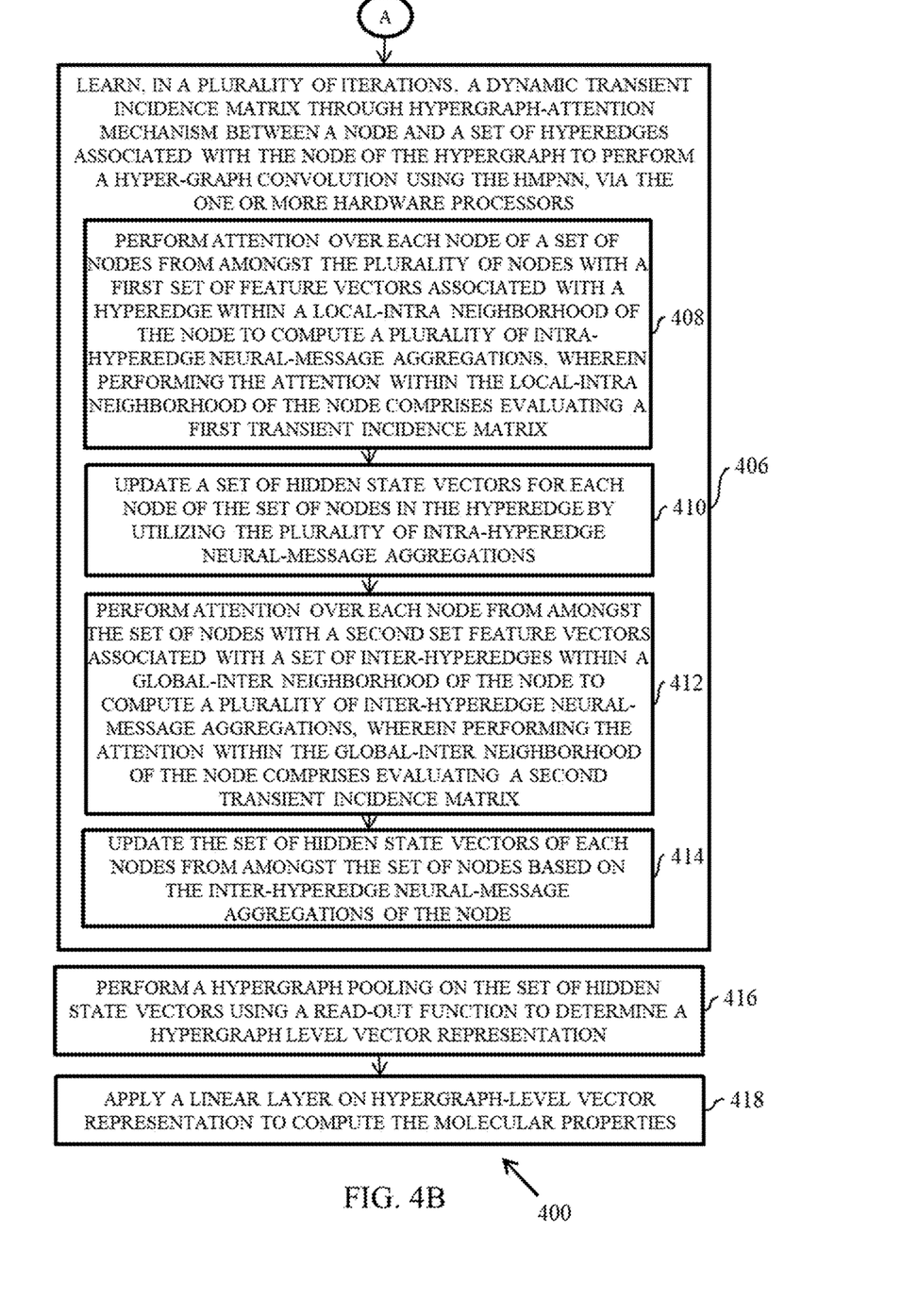
Figure 5:
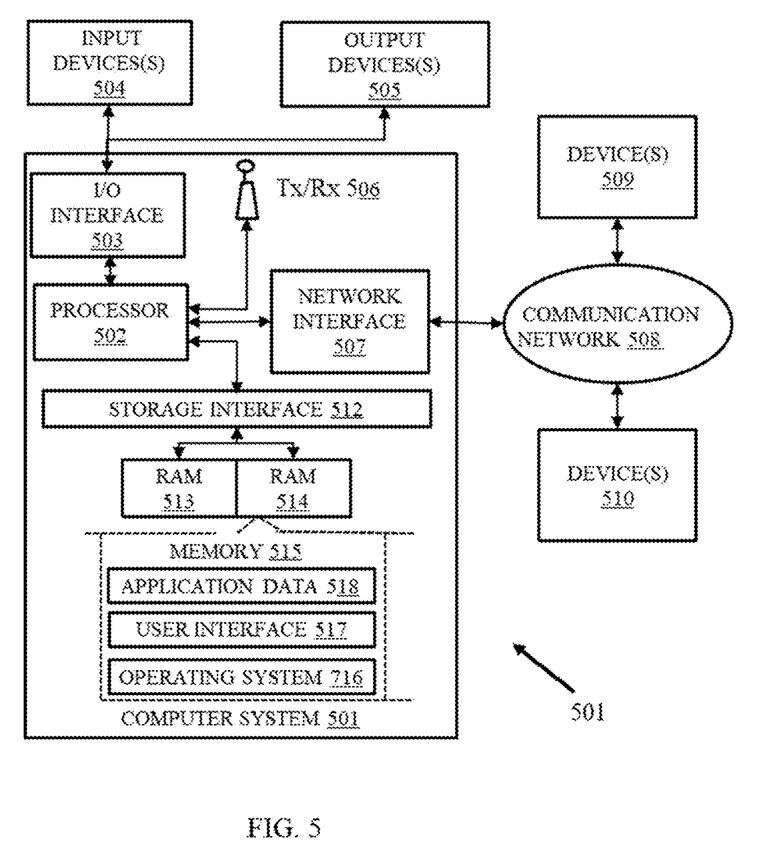
FIG. 5 is a block diagram of an exemplary computer system for implementing embodiments consistent with the present disclosure.

Referring now to the drawings, and more particularly to FIG. 3 through 5, where similar reference characters denote corresponding features consistently throughout the figures, there are shown preferred embodiments and these embodiments are described in the context of the following exemplary system and/or method.

FIG. 3 illustrates an example network implementation 300 of a system 302 for molecular property prediction using HyperGraph convolution based Message-Passing Neural Networks (HMPNNs) in accordance with example embodiment of present disclosure. With an increasing number of layers, each node abstract representations in a GCN layer converges to the graph's random walk limit distribution where the local node-neighborhood information is lost regardless of the nodes initial high-level representation. To alleviate such drawbacks, the disclosed system 302 represents a molecule as a hypergraph rather than a molecular graph (a 2-uniform hypergraph). A Hypergraph attention driven convolution, on molecular hypergraph results in learning efficient embeddings on the high-order molecular graph-structured data. By taking into account the transient incidence matrix, the induced inductive bias augments the scope of molecular hypergraph representation learning.

The disclosed system 302 facilitates in building a model to prognosticate the desired properties of organic molecules. The mathematical formulation of the problem is formally defined as, $f''(f(\mathcal{G}^*))=y$, and $\mathcal{G}^*$ refers to a molecular hypergraph $\mathcal{G}^{\mathcal{H}}$. Here, y denotes the target property to predict. $f:\eta \to \mathbb{R}^{|V^*|\times d}$ is a downstream mathematical function for evaluating the properties of interest, and learns the expressive low-dimensional abstract representations of the nodes in $\mathcal{G}^*$.

The disclosed system 302 leverages node-ordering invariant, read-out function (for example, Set2Set algorithm R': $\mathbb{R}^{|V^*|\times d} \to h_{\mathcal{G}^*}$) to perform graph-pooling, and to determine discriminative graph/hypergraph level embedding. $h_{\mathcal{G}^*}$. f": $h_{\mathcal{G}^*} \to \mathbb{R}$ s a downstream mathematical function for evaluating the chemical properties of interest. Here, d is the characteristic dimension of the node embedding.

The disclosed system 302 provides a supervised learning on drug-like potential molecules for use in effective drug discovery. It provides substantial prospects in diminishing the computational complexity which is a key desideratum for prognostication of molecular properties and aid in billion price tag cost reduction of developing a potential drug for treatment. The system 302 enables design variants for injective multi-set neural-network functions for message-generation and message pooling mechanism on hypergraph local and global neighborhood following the computational graph of each node in the given molecular graphs.

Although the present disclosure is explained considering that the system 302 is implemented on a server, it may be understood that the system 302 may also be implemented in a variety of computing systems 304, such as a laptop computer, a desktop computer, a notebook, a workstation, a cloud-based computing environment and the like. It will be understood that the system 302 may be accessed through one or more devices 306-1, 306-2 . . . 306-N, collectively referred to as devices 306 hereinafter, or applications residing on the devices 306. Examples of the devices 306 may include, but are not limited to, a portable computer, a personal digital assistant, a handheld device, a smartphone, a tablet computer, a workstation and the like. The devices 306 are communicatively coupled to the system 302 through a network 308.

In an embodiment, the network 308 may be a wireless or a wired network, or a combination thereof. In an example, the network 308 can be implemented as a computer network, as one of the different types of networks, such as virtual private network (VPN), intranet, local area network (LAN), wide area network (WAN), the internet, and such. The network 306 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 308 may include a variety of network devices, including routers, bridges, servers, computing devices, storage devices. The network devices within the network 308 may interact with the system 302 through communication links.

As discussed above, the system 302 may be implemented in a computing device 304, such as a hand-held device, a laptop or other portable computer, a tablet computer, a mobile phone, a PDA, a smartphone, and a desktop computer. The system 302 may also be implemented in a workstation, a mainframe computer, a server, and a network server. In an embodiment, the system 302 may be coupled to a data repository, for example, a repository 312. The repository 312 may store data processed, received, and generated by the system 302. In an alternate embodiment, the system 302 may include the data repository 312.

The network implementation 300 supports various connectivity options such as BLUETOOTH®, USB, ZIGBEE® and other cellular services. The network environment enables connection of devices 306 such as Smartphone with the server 304, and accordingly with the database 312 using any communication link including Internet, WAN, MAN, and so on. In an exemplary embodiment, the system 302 is implemented to operate as a stand-alone device. In another embodiment, the system 302 may be implemented to work as a loosely coupled device to a smart computing environment.

FIGS. 4A-4B illustrates a flow chart of a method 400 for molecular property prediction using hypergraph message passing neural network (HMPNN), in accordance with an example embodiment of present disclosure. Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 400 are described with help of system 102. However, the operations of the method 400 can be described and/or practiced by using any other system.

At step 402 of method 400, a database comprising a plurality of molecular graphs associated with a plurality of molecules is accessed via one or more hardware processors. The database includes an information associated with a plurality of molecules such that each molecule of the plurality of molecules is represented as a molecular graph. An example of a molecular graph is illustrated and described with reference to FIG. 3C.

At step 404 of method 400, each of the molecular graph is represented as an undirected hypergraph. As illustrated and described in FIG. 3C the undirected hypergraph includes a plurality of nodes and a plurality of hyperedges connecting the plurality of nodes. Hypergraph convolutions are designed to take $\mathcal{G}^{\mathcal{H}}=(V^H,\varepsilon^H)$ with $M^H(|V^H|)$ nodes and $N^H(|\varepsilon^H|)$ hyperedges as input. In contrast to a graph model, a hyperedge of the hypergraph model will bind over many vertices.

At step 406, the method 400 includes learning, in a plurality of iterations, a dynamic transient incidence matrix through hypergraph-attention mechanism between a node and a set of hyperedges associated with the node of the hypergraph to perform a hyper-graph convolution using the HMPNN.

The hypergraph $\mathcal{G}^{\mathcal{H}}$ is described by an incidence matrix $H^H \in \mathbb{R}^{M^H \times N^H}$. If $v_k \in V^H$ is connected by $\epsilon_j \in \varepsilon^H$ it implies the hyperedge $\epsilon_j$ is incident with a node $v_k$, thus $H_{kj}^H=1$ or else 0. Every hyperedge $\epsilon_j \in \varepsilon^H$ is associated with a weight $W_{jj}^H$ with all the weight entries cached in a scaling diagonal matrix $W^H \mathbb{R}^{N^H \times N^H}$. The node degree of the hypergraph $\mathcal{G}^{\mathcal{H}}$ is described as $D_{kk}{}^H = \Sigma_{j=1}{}^{N^H} W_{jj}{}^H H_{kj}{}^H$. The hyperedge degree of the hypergraph $\mathcal{G}^{\mathcal{H}}$ is defined as $B_{jj}{}^H = \Sigma_{k=1}{}^{M^H} H_{kj}{}^H$. Here, $D^H \in \mathbb{R}^{M^H \times M^H}$ and $B^H \in \mathbb{R}^{N^H \times N^H}$ are both diagonal matrices. The hypergraph convolution, is described as:

$$F_k^{(L+1)} = \sigma(\Sigma_{i=1}{}^{M^H} \Sigma_{j=1}{}^{N^H} H_{kj}{}^H H_{ij} W_{jj} F_l^{(L)} P). \tag{8}$$

Here, $F_k^{(L)}$ is the abstract representation of the k-th node in the (L)-th layer. $\sigma(\cdot)$ denotes denotes a non-linear tanh activation function.

$P \in \mathbb{R}^{F^{(L)} \times F^{(L+1)}}$ is the learnable weight matrix. The hypergraph convolution can be expressed in a matrix form as:

$$F^{(L+1)} = \sigma(H^H W^H H^{H^T} F^{(L)} P) \tag{9}$$

Here, $F^{(L)} \in \mathbb{R}^{M^H \times F^{(L)}}$ and $F^{(L-1)} \in \mathbb{R}^{M^H \times F^{(L+1)}}$ are the input of the (L)-th and (L+1)-th layer respectively. A symmetric normalization is put in to avoid exploding/vanishing gradient and thus, $$F^{(L+1)} = \sigma(D^{H^{-1/2}} H^H W^H B^{H^{-1}} H^{H^T} D^{H^{-1/2}} F^{(L)} P) \tag{10}$$

$F^{(L+1)}$ is differentiable with respect to $F^{(L)}$ and P.

Here, in the context of molecular hypergraphs $W_{ij}{}^H = \delta_{ij}$ is the identity matrix.

In an embodiment, the disclosed method includes performing the hypergraph attention whose sole objective is to learn the dynamic incidence matrix. The system learns the non-binary representation of the measure the degree of connectivity and is computed as below $$H_{kj} = \frac{\exp\left(\sigma\left(\mathcal{ATT}\left(F_k P, F_j^{\varepsilon^H} P\right)\right)\right)}{\sum_{k \in N_k} \exp\left(\sigma\left(\mathcal{ATT}\left(F_k P, F_s^{\varepsilon^H} P\right)\right)\right)} \tag{11}$$

Here, $\sigma(\cdot)$ is a non-linear activation function. $\mathcal{N}_k$ is the neighborhood hyperedge set of $v_k \in V^H$. $\mathcal{ATT}(\bullet)$ is an attention function that computes the pairwise attention coefficients between the given vertex and its associated hyperedge, defined as $$\mathcal{ATT}(F_k P, F_j^{\varepsilon^H} P) = a^T[(F_k P \| F_j^{\varepsilon^H} P) \cdot \sigma((F_k P)^T F_j^{\varepsilon^H} P)] \tag{12}$$

Here, $F^{\varepsilon^H}$ denotes the static-hyperedge feature matrix, and a is a weight vector used to output a scalar attention value.

The step 406 of learning the dynamic transient incidence matrix through the hypergraph-attention mechanism in an iteration from amongst the plurality of iterations is described further with reference to steps 408-414.

At step 408, the method 406 includes performing attention over each node of a set of nodes from amongst the plurality of nodes with a first set of feature vectors associated with a hyperedge within a local-intra neighborhood of the node to compute a plurality of intra-hyperedge neural-message aggregations. Herein, the local-intra neighborhood of the node refers to the set of nodes within the same hyperedge as the node. Mathematically, the local-intra neighborhood of the node $v_l \in V^H$ E $V^H$ for any hyperedge $\epsilon_j \in \varepsilon^H$ is defined as the set of nodes $v_l$ belonging to $\epsilon_j$.

Performing the attention within the local-intra neighborhood of the node includes evaluating a first transient incidence matrix. The first transient incidence matrix fill refers to the transient matrix learnt by computing pairwise attention coefficients between the node and its associated hyperedge.

At step 410, the method 406 includes updating a set of hidden state vectors for the set of nodes in the hyperedge by utilizing the plurality of intra-hyperedge neural-message aggregations. Herein, the term $\Sigma_{j=1}{}^{M^H} H_{ij}{}^H F_l^{(L)} P$ updates the hidden state vectors of the nodes in a given hyperedge, j in the corresponding hypergraph. The term $\Sigma_{j=1}{}^{M^H} H_{ij}{}^H F_l^{(L)} P$ denotes the intra-hyperedge neural-message aggregations.

At step 412, the method 406 performing attention over each node from amongst the set of nodes with a second set feature vectors associated with a set of inter-hyperedges within a global-inter neighborhood of the node to compute a plurality of inter-hyperedge neural-message aggregations. Performing the attention within the global-inter neighborhood of the node comprises evaluating a second transient incidence matrix. At step 414, the method 406 includes updating the set of hidden state vectors of each nodes from amongst the set of nodes based on the inter-hyperedge neural-message aggregations of the node.

Herein, the global-inter neighborhood of the node refers to the nodes in neighboring hyperedges of the hyperedge belonging to the node.

Mathematically, $\Sigma_{j=1}{}^{N^H} H_{kj}{}^H \Sigma_{l=1}{}^{M^H} H_{ij}{}^H F_l^{(L)} P$ denotes the inter-hyperedge neural-message global-neighborhood aggregations. Herein the second transient incidence matrix $H_{kj}{}^H$ refers to the transient matrix learnt by computing pairwise attention coefficients between the node and one or more nodes in one or more hyperedges in the neighborhood of the node's hyperedge.

The hypergraph convolution operator is interleaved with a read-out function to learn discriminative hypergraph embeddings in an end-to-end training by optimizing it through a gradient descent algorithm. At step 416, the method 400 includes performing a hypergraph pooling on the set of hidden state vectors using a read-out function to determine a hypergraph-level vector representation. At step 418, the method 400 includes applying a linear layer on hypergraph-level vector representation to compute the molecular properties. For example, a read-out function (for example, Set2Set algorithm R': $\mathbb{R}^{|v^*| \times d} \to h_{\mathcal{G}^*}$) may be used to perform graph-pooling, and to determine discriminative graph/hypergraph level embedding. $h_{\mathcal{G}^*}$. $f'': h_{\mathcal{G}^*} \to \mathbb{R}$ s a downstream mathematical function for evaluating the chemical properties of interest. Here, d is the characteristic dimension of the node embedding.

An algorithm illustrating the disclosed method is presented below:

Algorithm: Hypergraph message passing neural network

1: Input Feature Training set: data.x, data.edgeindex, data.edgeattr
2: Input Target Label : data.y
3: Regularization Term: Apply dropout on data.x, data.edgeindex, & data.edgeattr
4: Message-Passing Phase
5: for t ≤ T do
6: Forward Pass & Vertex Update: Perform HyperGraph Convolution
7: end for
8: Read out Operation: Apply Set2Set Algorithm
9: Linear Layer
10: Return Graph level output: Predict DFT target properties FIG. 5 is a block diagram of an exemplary computer system 501 for implementing embodiments consistent with the present disclosure. The computer system 501 may be implemented in alone or in combination of components of the system 302 (FIG. 3). Variations of computer system 501 may be used for implementing the devices included in this disclosure. Computer system 501 may comprise a central processing unit ("CPU" or "hardware processor") 502. The hardware processor 502 may comprise at least one data processor for executing program components for executing user- or system-generated requests. The processor may include specialized processing units such as integrated system (bus) controllers, memory management control units, floating point units, graphics processing units, digital signal processing units, etc. The processor may include a microprocessor, such as AMD ATHLON™, DURON™ or OPTERON™, ARM's application, embedded or secure processors, IBM POWERPC™ INTEL's Core, ITANIUM™, XEON™, CELERON™ or other line of processors, etc. The processor 502 may be implemented using mainframe, distributed processor, multi-core, parallel, grid, or other architectures. Some embodiments may utilize embedded technologies like application specific integrated circuits (ASICs), digital signal processors (DSPs), Field Programmable Gate Arrays (FPGAs), etc. The processor 502 may be a multi-core multi-threaded processor.

Processor 502 may be disposed in communication with one or more input/output (I/O) devices via I/O interface 503. The I/O interface 503 may employ communication protocols/methods such as, without limitation, audio, analog, digital, monoaural, RCA, stereo, TEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, BLUETOOTH®, cellular (e.g., code-division multiple access (CDMA), high-speed packet access (HSPA+), global system for mobile communications (GSM), long-term evolution (LTE), WIMAX, or the like), etc.

Using the I/O interface 503, the computer system 501 may communicate with one or more I/O devices. For example, the input device 504 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc.

Output device 505 may be a printer, fax machine, video display (e.g., cathode ray tube (CRT), liquid crystal display (LCD), light-emitting diode (LED), plasma, or the like), audio speaker, etc. In some embodiments, a transceiver 506 may be disposed in connection with the processor 502. The transceiver may facilitate various types of wireless transmission or reception. For example, the transceiver may include an antenna operatively connected to a transceiver chip (e.g., TEXAS INSTRUMENTS WILINK™ WL1283, BROADCOM BCM4750IUB8, INFINEON TECHNOLOGIES X-GOLD™ 618-PMB9800, or the like), providing IEEE 802.1 1a/b/g/n, BLUETOOTH®, FM, global positioning system (GPS), 2G/3G HSDPA/HSUPA communications, etc.

In some embodiments, the processor 502 may be disposed in communication with a communication network 508 via a network interface 507. The network interface 507 may communicate with the communication network 508. The network interface may employ connection protocols including, without limitation, direct connect, Ethernet (e.g., twisted pair 10/100/1000 Base T), transmission control protocol/internet protocol (TCP/IP), token ring, IEEE 802.1 1a/b/g/n/x, etc. The communication network 508 may include, without limitation, a direct interconnection, local area network (LAN), wide area network (WAN), wireless network (e.g., using Wireless Application Protocol), the Internet, etc. Using the network interface 507 and the communication network 508, the computer system 501 may communicate with devices 509 and 510. These devices may include, without limitation, personal computer(s), server(s), fax machines, printers, scanners, various mobile devices such as cellular telephones, smartphones (e.g., APPLE IPHONE®, BLACKBERRY®, ANDROID-based phones, etc.), tablet computers, eBook readers (AMAZON KINDLE™ NOOK™, etc.), laptop computers, notebooks, gaming consoles (MICROSOFT XBOX®, NINTENDO DS, SONY PLAYSTATION®, etc.), or the like. In some embodiments, the computer system 501 may itself embody one or more of these devices.

In some embodiments, the processor 502 may be disposed in communication with one or more memory devices (e.g., RAM 513, ROM 514, etc.) via a storage interface 512. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc. Variations of memory devices may be used for implementing, for example, any databases utilized in this disclosure.

The memory devices may store a collection of programs or database components, including, without limitation, an operating system 516, user interface application 517, user/application data 518 (e.g., any data variables or data records discussed in this disclosure), etc. The operating system 516 may facilitate resource management and operation of the computer system 501. Examples of operating systems include, without limitation, APPLE MACINTOSH® OS X, UNIX, UNIX-like system distributions (e.g., Berkeley Software Distribution (BSD), FREEBSD, NETBSD, OpenBSD, etc.), Linux distributions (e.g., RED HAT, UBUNTU, KUBUNTU, etc.), IBM® OS/2, MICROSOFT WINDOWS® (XP, Vista/7/8, etc.), APPLE® IOS, GOOGLE ANDROID®, BLACKBERRY® OS, or the like. User interface 517 may facilitate display, execution, interaction, manipulation, or operation of program components through textual or graphical facilities. For example, user interfaces may provide computer interaction interface elements on a display system operatively connected to the computer system 501, such as cursors, icons, check boxes, menus, scrollers, windows, widgets, etc. Graphical user interfaces (GUIs) may be employed, including, without limitation, APPLE MACINTOSH® operating systems' AQUA, IBM® OS/2, MICROSOFT WINDOWS® (e.g., Aero, Metro, etc.), UNIX X-Windows, web interface libraries (e.g., ActiveX, JAVA, JAVASCRIPT, AJAX, HTML, ADOBE Flash, etc.), or the like.

In some embodiments, computer system 501 may store user/application data 518, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, structured text file (e.g., XML), table, or as hand-oriented databases (e.g., using HandStore, Poet, Zope, etc.). Such databases may be consolidated or distributed, sometimes among various computer systems discussed above. It is to be understood that the structure and operation of any computer or database component may be combined, consolidated, or distributed in any working combination.

Additionally, in some embodiments, (the server, messaging and instructions transmitted or received may emanate from hardware, including operating system, and program code (i.e., application code) residing in a cloud implementation. Further, it should be noted that one or more of the systems and methods provided herein may be suitable for cloud-based implementation. For example, in some embodiments, some or all of the data used in the disclosed methods may be sourced from or stored on any cloud computing platform.

Example Scenario

Every atom in a given molecule in the known QM-8 dataset is associated with diverse characteristic features at hand that comprehend both the possessions of the electrons in the atom and the edge-types namely, single, double, triple bond or it's a part of an aromatic ring in which the atom is binded. The hydrogen atoms are assumed to be explicit nodes in the graph. The atom (node) attributes and their associated representation include the atom type (one-hot), atomic number (integer), acceptor (binary), donor (binary), aromatic (binary), hybridization (one-hot or null) and the number of hydrogen atoms (integer). The remaining are one-hot encoding descriptions of the bond kind. The edge (bond) characteristic feature attributes include only the bond type (one-hot), aromatic ring (binary), and the Euclidean distance between nodes (vector). Here the Euclidean separation distance are pre-determined by the DFT simulations.

For comparison with the recent advances in graph networks, that comprises Graph convolution networks (GCN-FP), Gated graph neural networks (GGNN), Diffusion convolutional neural networks (DCNN), Chebyshev networks (ChebyNet), Graph convolutional networks (GCN), message passing neural networks (MPNN), and Graph attention networks (GAT). Then performance of all the algorithms was benchmarked on the QM8 quantum chemistry dataset based on a supervised regression task of molecule chemical property prediction task. This dataset is based on a study of computational quantum mechanical modeling calculations of electronic spectra and electronic energy of small molecules. The objective of the work is to predict 16 Density Functional Theory (DFT) based simulations properties per molecular graph. There is a comprehensive number of 21786 molecular graphs in the QM8 dataset. We break the QM8 dataset to possess 17428, 2179 and, 2179 molecular graphs for training, validation, and testing respectively. Following mean squared error (MSE) is utilized as the loss function and the learnable weights are overhauled by the backpropagation algorithm during training. The mean absolute error (MAE) is leveraged as the evaluation metric.

The validation and test MAEs are shown in Table 1. The results from the baselines are reproduced.

TABLE 1

The table reports the Mean absolute error (MAE) metric evaluated on the QM8 dataset

| Methods | Validation MAE (X1.0e$^{-3}$) | Test MAE (X1.0e$^{-3}$) |
| --- | --- | --- |
| GCN-FP | 15.06 ± 0.04 | 14.8 ± 0.09 |
| GGNN | 12.94 ± 0.05 | 12.67 ± 0.22 |
| DCNN | 10.14 ± 0.05 | 9.97 ± 0.09 |
| ChebyNet | 10.24 ± 0.06 | 10.07 ± 0.09 |
| GCN | 11.68 ± 0.09 | 11.41 ± 0.1 |
| MPNN | 11.16 ± 0.13 | 11.08 ± 0.11 |
| GraphSAGE | 13.19 ± 0.04 | 12.95 ± 0.11 |
| GPNN | 12.81 ± 0.8 | 12.39 ± 0.77 |
| GAT | 11.39 ± 0.09 | 11.02 ± 0.06 |
| LanczosNet | 9.65 ± 0.19 | 9.58 ± 0.14 |
| AdaLanczosNet | 10.1 ± 0.22 | 9.97 ± 0.2 |
| PEIPNP | 6.72 ± 0.05 | 6.94 ± 0.06 |
| HA-MPA | 5.98 ± 0.11 | 6.13 ± 0.14 |

The disclosed method includes an appropriate choice of the message generating update, and output functions have a useful inductive bias for the hypergraph-level representation learning. The effectiveness of learning in the depiction of the task pertinent chemical hypergraph substructures into augmented expressiveness of the node embeddings on the graph/hypergraph topology leads to improvements in property prediction tasks accuracies. The HyperGraph attention-driven HyperGraph Convolution achieves state-of-the-art results in the Quantum chemistry property prediction task. The comparative study performed with the existing state-of-the-art algorithms, show that the disclosed method and system outperforms several strong baselines and reinforce the effectiveness of our novel unifying formalism.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for molecular property prediction for drug discovery using a hypergraph message passing neural network (HMPNN), the method comprising:
   accessing a database comprising information associated with a plurality of molecules, via one or more hardware processors, wherein each molecule of the plurality of molecules represented as a molecular graph, and wherein the plurality of molecules include potential molecules;
   representing each of the molecular graph as an undirected hypergraph, via the one or more hardware processors, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix;
   learning, in a plurality of iterations, a dynamic transient incidence matrix through a hypergraph-attention mechanism between a node and a set of hyperedges associated with the node of the hypergraph to perform a hyper-graph convolution using the HMPNN, via the one or more hardware processors, wherein learning the dynamic transient incidence matrix through the hypergraph-attention mechanism in an iteration from amongst the plurality of iterations comprises:
      performing attention over each node of a set of nodes from amongst the plurality of nodes with a first set of feature vectors associated with a hyperedge within a local-intra neighborhood of the node to compute a plurality of intra-hyperedge neural-message aggregations, wherein performing the attention within the local-intra neighborhood of the node comprises evaluating a first transient incidence matrix, and wherein the first transient incidence matrix refers to a transient matrix learnt by computing pairwise attention coefficients between the node and an hyperedge belonging to the node;
      updating a set of hidden state vectors for each node of the set of nodes in the hyperedge by utilizing the plurality of intra-hyperedge neural-message aggregations;
      performing attention over each node from amongst the set of nodes with a second set feature vectors associated with a set of inter-hyperedges within a global-inter neighborhood of the node to compute a plurality of inter-hyperedge neural-message aggregations, wherein the global-inter neighborhood of the node refers to nodes in neighboring hyperedges of the hyperedge belonging to the node, wherein performing the attention within the global-inter neighborhood of the node comprises evaluating a second transient incidence matrix, and wherein the second transient incidence matrix refers to a transient matrix learnt by computing pairwise attention coefficients between the node and one or more nodes in one or more hyperedges in neighborhood of the hyperedge belonging to the node; and
      updating the set of hidden state vectors of each node from amongst the set of nodes based on the plurality of inter-hyperedge neural-message aggregations of the node;
   performing, via the one or more hardware processors, a hypergraph pooling on the set of hidden state vectors using a read-out function to determine a hypergraph level vector representation, wherein a hypergraph convolution operator is interleaved with the read-out function to learn discriminative hypergraph embeddings in an end-to-end training by optimizing the read-out function through a gradient descent algorithm;
   preventing, via the one or more hardware processors, over-smoothing of the learnt discriminative hypergraph embeddings for vertices with higher valency using an anti-smoothing weighting mechanism; and
   applying, via the one or more hardware processors, a linear layer on the hypergraph-level vector representation to compute the molecular properties for the drug discovery, via the one or more hardware processors.

2. The processor implemented method of claim 1, wherein the plurality of inter-hyperedge neural-message aggregations of the node are denoted by the equation:

$$\sum_{j=1}^{M^H} H_{ij}^H F_l^{(L)} P$$

where, $H_{ij}^H$ is the first transient incidence matrix,
$F_l^{(L)}$ is abstract representation of the l-th node from amongst the plurality of nodes in (L)-th iteration, and
P is a learnable weight matrix.

3. A system for molecular property prediction for drug discovery using a hypergraph message passing neural network (HMPNN), comprising:
   a memory storing instructions;
   one or more communication interfaces; and one or more hardware processors coupled to the memory via the one or more communication interfaces, wherein the one or more hardware processors are configured by the instructions to:

access a database comprising an information associated with a plurality of molecules, wherein each molecule of the plurality of molecules represented as a molecular graph, and wherein the plurality of molecules include drug-like potential molecules;

represent each of the molecular graph as an undirected hypergraph, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix;

learn, in a plurality of iterations, a dynamic transient incidence matrix through a hypergraph-attention mechanism between a node and a set of hyperedges associated with the node of the hypergraph to perform a hyper-graph convolution using the HMPNN, wherein to learn the dynamic transient incidence matrix through the hypergraph-attention mechanism in an iteration from amongst the plurality of iterations, the one or more hardware processors are configured by the instructions to:

perform attention over each node of a set of nodes from amongst the plurality of nodes with a first set of feature vectors associated with a hyperedge within a local-intra neighborhood of the node to compute a plurality of intra-hyperedge neural-message aggregations, wherein performing the attention within the local-intra neighborhood of the node comprises evaluating a first transient incidence matrix, and wherein the first transient incidence matrix refers to a transient matrix learnt by computing pairwise attention coefficients between the node and an hyperedge belonging to the node;

update a set of hidden state vectors for each node of the set of nodes in the hyperedge by utilizing the plurality of intra-hyperedge neural-message aggregations;

perform attention over each node from amongst the set of nodes with a second set feature vectors associated with a set of inter-hyperedges within a global-inter neighborhood of the node to compute a plurality of inter-hyperedge neural-message aggregations, wherein the global-inter neighborhood of the node refers to nodes in neighboring hyperedges of the hyperedge belonging to the node, wherein performing the attention within the global-inter neighborhood of the node comprises evaluating a second transient incidence matrix, and wherein the second transient incidence matrix refers to a transient matrix learnt by computing pairwise attention coefficients between the node and one or more nodes in one or more hyperedges in neighborhood of the hyperedge belonging to the node; and update the set of hidden state vectors of each node from amongst the set of nodes based on the plurality of inter-hyperedge neural-message aggregations of the node;

perform a hypergraph pooling on the set of hidden state vectors using a read-out function to determine a hypergraph level vector representation, wherein a hypergraph convolution operator is interleaved with the read-out function to learn discriminative hypergraph embeddings in an end-to-end training by optimizing the read-out function through a gradient descent algorithm;

prevent over-smoothing of the learnt discriminative hypergraph embeddings for vertices with higher valency using an anti-smoothing weighting mechanism; and apply a linear layer on the hypergraph-level vector representation to compute the molecular properties for the drug discovery.

4. A system for molecular property prediction for drug discovery using a hypergraph message passing neural network (HMPNN), comprising:

a memory storing instructions;

one or more communication interfaces; and one or more hardware processors coupled to the memory via the one or more communication interfaces, wherein the one or more hardware processors are configured by the instructions to:

access a database comprising an information associated with a plurality of molecules, wherein each molecule of the plurality of molecules represented as a molecular graph, and wherein the plurality of molecules include drug-like potential molecules;

represent each of the molecular graph as an undirected hypergraph, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix;

learn, in a plurality of iterations, a dynamic transient incidence matrix through a hypergraph-attention mechanism between a node and a set of hyperedges associated with the node of the hypergraph to perform a hyper-graph convolution using the HMPNN, wherein to learn the dynamic transient incidence matrix through the hypergraph-attention mechanism in an iteration from amongst the plurality of iterations, the one or more hardware processors are configured by the instructions to:

perform attention over each node of a set of nodes from amongst the plurality of nodes with a first set of feature vectors associated with a hyperedge within a local-intra neighborhood of the node to compute a plurality of intra-hyperedge neural-message aggregations, wherein performing the attention within the local-intra neighborhood of the node comprises evaluating a first transient incidence matrix, and wherein the first transient incidence matrix refers to a transient matrix learnt by computing pairwise attention coefficients between the node and an hyperedge belonging to the node;

update a set of hidden state vectors for each node of the set of nodes in the hyperedge by utilizing the plurality of intra-hyperedge neural-message aggregations;

perform attention over each node from amongst the set of nodes with a second set feature vectors associated with a set of inter-hyperedges within a global-inter neighborhood of the node to compute a plurality of inter-hyperedge neural-message aggregations, wherein the global-inter neighborhood of the node refers to nodes in neighboring hyperedges of the hyperedge belonging to the node, wherein performing the attention within the global-inter neighborhood of the node comprises evaluating a second transient incidence matrix, and wherein the second transient incidence matrix refers to a transient matrix learnt by computing pairwise attention coefficients between the node and one or more nodes in one or more hyperedges in neighborhood of the hyperedge belonging to the node; and update the set of hidden state vectors of each nodes from amongst the set of nodes based on the plurality of inter-hyperedge neural-message aggregations of the node;

perform a hypergraph pooling on the set of hidden state vectors using a read-out function to determine a hypergraph level vector representation, wherein a hypergraph convolution operator is interleaved with the read-out function to learn discriminative hypergraph embeddings in an end-to-end training by optimizing the read-out function through a gradient descent algorithm;

prevent over-smoothing of the learnt discriminative hypergraph embeddings for vertices with higher valency using an anti-smoothing weighting mechanism; and apply a linear layer on the hypergraph-level vector representation to compute the molecular properties for the drug discovery.

5. The system of claim 4, wherein the plurality of inter-hyperedge neural-message aggregations of the node are donated by the equation $$\sum_{j=1}^{M^H} H_{ij}^H F_l^{(L)} P$$

where, $H_{ij}^H$ is the first transient incidence matrix,
$F_l^{(L)}$ is abstract representation of the l-th node from amongst the plurality of nodes in (L)-th iteration, and
P is a learnable weight matrix.

6. The system of claim 4, wherein the plurality of inter-hyperedge neural-message aggregations of the node are denoted by the equation:

$$\sum_{j=1}^{N^H} H_{kj}^H \sum_{l=1}^{M^H} H_{ij}^H F_l^{(L)} P$$

where, $H_{kj}^H$ is the second transient incidence matrix,
$H_{ij}^H$ is the first transient incidence matrix,
$F_l^{(L)}$ is abstract representation of the l-th node from amongst the plurality of nodes in (L)-th iteration, and
P is a learnable weight matrix.

7. One or more non-transitory machine-readable information storage mediums comprising one or more instructions which when executed by one or more hardware processors cause:

accessing a database comprising information associated with a plurality of molecules, via one or more hardware processors, wherein each molecule of the plurality of molecules represented as a molecular graph, and wherein the plurality of molecules include potential molecules;

representing each of the molecular graph as an undirected hypergraph, via the one or more hardware processors, wherein the undirected hypergraph comprises a plurality of nodes and a plurality of hyperedges connecting the plurality of nodes, and wherein each hyperedge is associated with a weight of the plurality of hyperedges of the molecular graph cached in a scaling diagonal matrix;

learning, in a plurality of iterations, a dynamic transient incidence matrix through a hypergraph-attention mechanism between a node and a set of hyperedges associated with the node of the hypergraph to perform a hyper-graph convolution using the HMPNN, via the one or more hardware processors, wherein learning the dynamic transient incidence matrix through the hypergraph-attention mechanism in an iteration from amongst the plurality of iterations comprises:

performing attention over each node of a set of nodes from amongst the plurality of nodes with a first set of feature vectors associated with a hyperedge within a local-intra neighborhood of the node to compute a plurality of intra-hyperedge neural-message aggregations, wherein performing the attention within the local-intra neighborhood of the node comprises evaluating a first transient incidence matrix, and wherein the first transient incidence matrix refers to a transient matrix learnt by computing pairwise attention coefficients between the node and an hyperedge belonging to the node;

updating a set of hidden state vectors for each node of the set of nodes in the hyperedge by utilizing the plurality of intra-hyperedge neural-message aggregations;

performing attention over each node from amongst the set of nodes with a second set feature vectors associated with a set of inter-hyperedges within a global-inter neighborhood of the node to compute a plurality of inter-hyperedge neural-message aggregations, wherein the global-inter neighborhood of the node refers to nodes in neighboring hyperedges of the hyperedge belonging to the node, wherein performing the attention within the global-inter neighborhood of the node comprises evaluating a second transient incidence matrix, and wherein the second transient incidence matrix refers to a transient matrix learnt by computing pairwise attention coefficients between the node and one or more nodes in one or more hyperedges in neighborhood of the hyperedge belonging to the node; and updating the set of hidden state vectors of each node from amongst the set of nodes based on the plurality of inter-hyperedge neural-message aggregations of the node;

performing, via the one or more hardware processors, a hypergraph pooling on the set of hidden state vectors using a read-out function to determine a hypergraph level vector representation, wherein a hypergraph convolution operator is interleaved with the read-out function to learn discriminative hypergraph embeddings in an end-to-end training by optimizing the read-out function through a gradient descent algorithm;

preventing, via the one or more hardware processors, over-smoothing of the learnt discriminative hypergraph embeddings for vertices with higher valency using an anti-smoothing weighting mechanism; and applying, via the one or more hardware processors, a linear layer on the hypergraph-level vector representation to compute the molecular properties for the drug discovery, via the one or more hardware processors.

8. The one or more non-transitory machine readable information storage mediums of claim 7, wherein the plurality of inter-hyperedge neural-message aggregations of the node are denoted by the equation:

$$\sum_{j=1}^{M^H} H_{lj}^H F_l^{(L)} P$$

where, $H_{ij}^H$ is the first transient incidence matrix,
$F_l^{(L)}$ is abstract representation of the l-th node from amongst the plurality of nodes in (L)-th iteration, and
P is a learnable weight matrix.

9. The one or more non-transitory machine readable information storage mediums of claim 7, wherein the plurality of inter-hyperedge neural-message aggregations of the node are denoted by the equation:

$$\sum_{j=1}^{N^H} H_{kj}^H \sum_{l=1}^{M^H} H_{lj}^H F_l^{(L)} P$$

where, $H_{ij}^H$ is the second transient incidence matrix,
$H_{ij}^H$ is the first transient incidence matrix,
$F_l^{(L)}$ is abstract representation of the l-th node from amongst the plurality of nodes in (L)-th iteration, and
P is a learnable weight matrix.

* * * * *